(12) United States Patent
Yasuhara et al.

(10) Patent No.: US 8,191,405 B2
(45) Date of Patent: Jun. 5, 2012

(54) SOLVENT DELIVERY DEVICE AND ANALYTICAL SYSTEM

(75) Inventors: Naoya Yasuhara, Hitachinaka (JP); Hironori Kaji, Hitachinaka (JP); Kimihiko Ishii, Hitachinaka (JP); Hiroyuki Wada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 590 days.

(21) Appl. No.: 12/359,381

(22) Filed: Jan. 26, 2009

(65) Prior Publication Data

US 2009/0193879 A1    Aug. 6, 2009

(30) Foreign Application Priority Data

Jan. 31, 2008 (JP) ................................. 2008-020043

(51) Int. Cl.
*G01N 1/00* (2006.01)
(52) U.S. Cl. ....................................................... 73/61.56
(58) Field of Classification Search .......................... None
See application file for complete search history.

(56) References Cited

U.S. PATENT DOCUMENTS

| | | | | |
|---|---|---|---|---|
| 4,131,393 A | * | 12/1978 | Magnussen, Jr. | ............... 417/22 |
| 4,311,586 A | * | 1/1982 | Baldwin et al. | ............... 210/101 |
| 4,595,495 A | * | 6/1986 | Yotam et al. | ................... 210/101 |
| 4,797,207 A | * | 1/1989 | Honganen et al. | ......... 210/198.2 |
| 4,883,409 A | * | 11/1989 | Strohmeier et al. | ............ 417/43 |
| 6,997,683 B2 | * | 2/2006 | Allington et al. | ............... 417/18 |
| 2004/0108273 A1 | * | 6/2004 | Richardson et al. | .......... 210/656 |
| 2005/0084386 A1 | | 4/2005 | Mori et al. | |
| 2007/0000312 A1 | * | 1/2007 | Weissgerber | ................ 73/61.56 |

FOREIGN PATENT DOCUMENTS

| | | |
|---|---|---|
| JP | 2001-254683 | 9/2001 |
| JP | 3709409 | 8/2005 |

\* cited by examiner

*Primary Examiner* — Robert R Raevis

(74) *Attorney, Agent, or Firm* — Antonelli, Terry, Stout & Kraus, LLP.

(57) ABSTRACT

Disclosed herein is a stable solvent delivery device capable of delivering solvent both at high pressure and at constant flow rate. A solvent delivery device comprises a plurality of plungers which reciprocate in the respective pump chambers including an eluent charge side pump chamber and an eluent discharge side pump chamber, a motor to reciprocate these plungers, a control unit to control the operation of the motor, valves which are respectively set at the eluent inlet and outlet of the eluent charge side pump chamber, a first sensor to measure the quantity of load received by the plunger in the eluent charge side pump chamber, and a second sensor to measure the pressure of the eluent discharged from the eluent discharge side pump chamber.

8 Claims, 3 Drawing Sheets

SOLVENT DELIVERY DEVICE AND ANALYTICAL SYSTEM

BACKGROUND OF THE INVENTION

1. Field of the Invention

The present invention relates to a liquid delivery device which delivers liquid. More particularly, it relates to a solvent delivery device which delivers eluent in an analytical system such as a liquid chromatograph.

2. Description of the Related Art

In liquid chromatography, it is ideal that a solvent delivery device always deliver eluent at a constant flow rate. If the flow rate is not constant, the analysis accuracy is lowered. However, it is common that the rate of flow from a solvent delivery device periodically changes (hereinafter this phenomenon being termed pulsation).

An example of the prior art techniques intended to reduce pulsations is described in Japanese Patent No. 3709409. However, this technique might face a problem if applied to a solvent delivery device in such an analytical system as a liquid chromatograph where solvent must be delivered at very high pressure. Specifically, this is because providing a pressure sensor increases the volume of eluent to be compressed. If this volume is so large that the eluent cannot fully be compressed, it may be impossible to deliver the eluent at a constant flow rate. Here, "very high pressure" means such a high pressure that the eluent is considerably compressed at the pressure. For example, if the eluent is methanol and delivered at 60 MPa, the methanol reduces 6.4% in volume as compared with its volume before compressed.

In a solvent delivery device disclosed in JP-A-2001-254683, a load sensor is used to reduce the volume of eluent to be compressed and the volume of eluent to be compressed is small. However, this does not contribute to reducing pulsations since the quantity of load measured by the load sensor is not related to the pressure of the eluent.

SUMMARY OF THE INVENTION

The present invention provides a stable solvent delivery device capable of delivering solvent both at high pressure and at a constant flow rate.

According to one aspect of the present invention, there is provided a solvent delivery device comprising: a plurality of plungers which reciprocate in respective pump chambers; a motor which is used to reciprocate the plungers; a control unit which controls the operation of the motor; check valves which are respectively disposed at an eluent inlet and an eluent outlet of the eluent charge side pump chamber; a first sensor which measures the quantity of load received by the plunger; and a second sensor which measures the pressure of the eluent discharged from the eluent discharge side pump chamber.

According to another aspect of the present invention, the eluent discharge flow rate is controlled based on the output signals respectively of the first sensor and second sensor.

According to another aspect of the present invention, the motor is controlled based on the output signals respectively of the first sensor and second sensor.

The above-mentioned and other aspects of the present invention will be described by the present specification and the drawings.

According to an embodiment of the present invention, it is possible to provide a stable solvent delivery device capable of delivering solvent both at very high pressure and at a constant flow rate.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Figure 2:
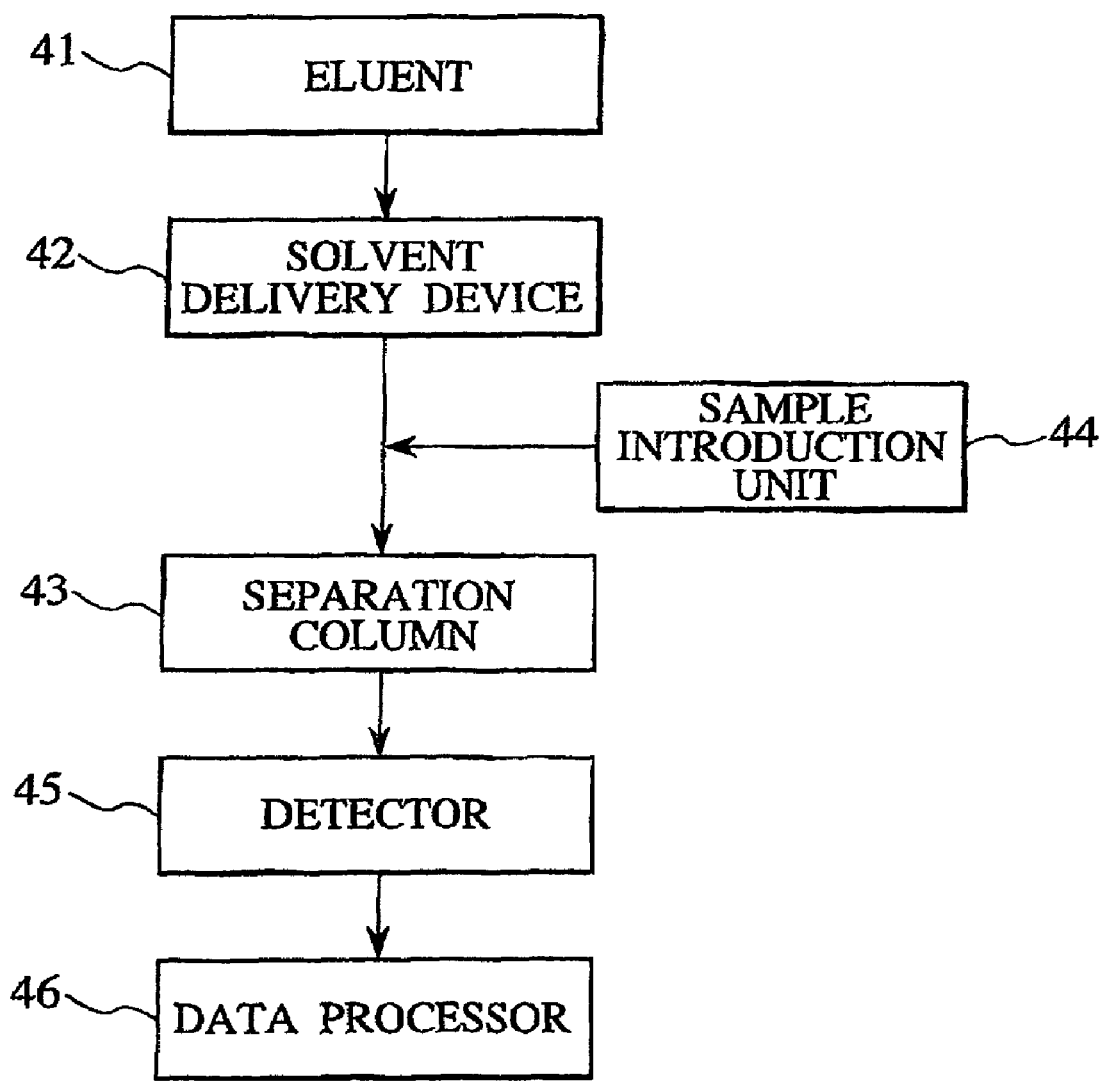
FIG. 2 schematically shows a liquid chromatograph where the solvent delivery device of the present invention is applied.

FIG. 2 shows an example of a liquid chromatograph used where the present invention is implemented. Eluent 41 is delivered to a separation column 43 by a solvent delivery device 42. A sample is introduced into the separation column 43 by a sample introduction device 44. As the sample passes through the separation column 43, components of the sample separate from each other. The separated sample components are detected by a detector 45. Signals concerning the detected sample components are sent to a data processor 46 where necessary processing is performed. After adding to the eluent a certain pressure which depends on the analysis, the solvent delivery device 42 discharges and delivers the eluent. If the eluent discharge pressure is constant, the flow rate is also constant. It is ideal for the solvent delivery device 42 to deliver the eluent always at the same flow rate. If the flow rate is not constant, the analysis accuracy lowers. However, it is common that such a solvent delivery device periodically changes the flow rate (hereinafter this phenomenon being termed pulsation). A solvent delivery device which solves the pulsation problem is described below.

Figure 1:
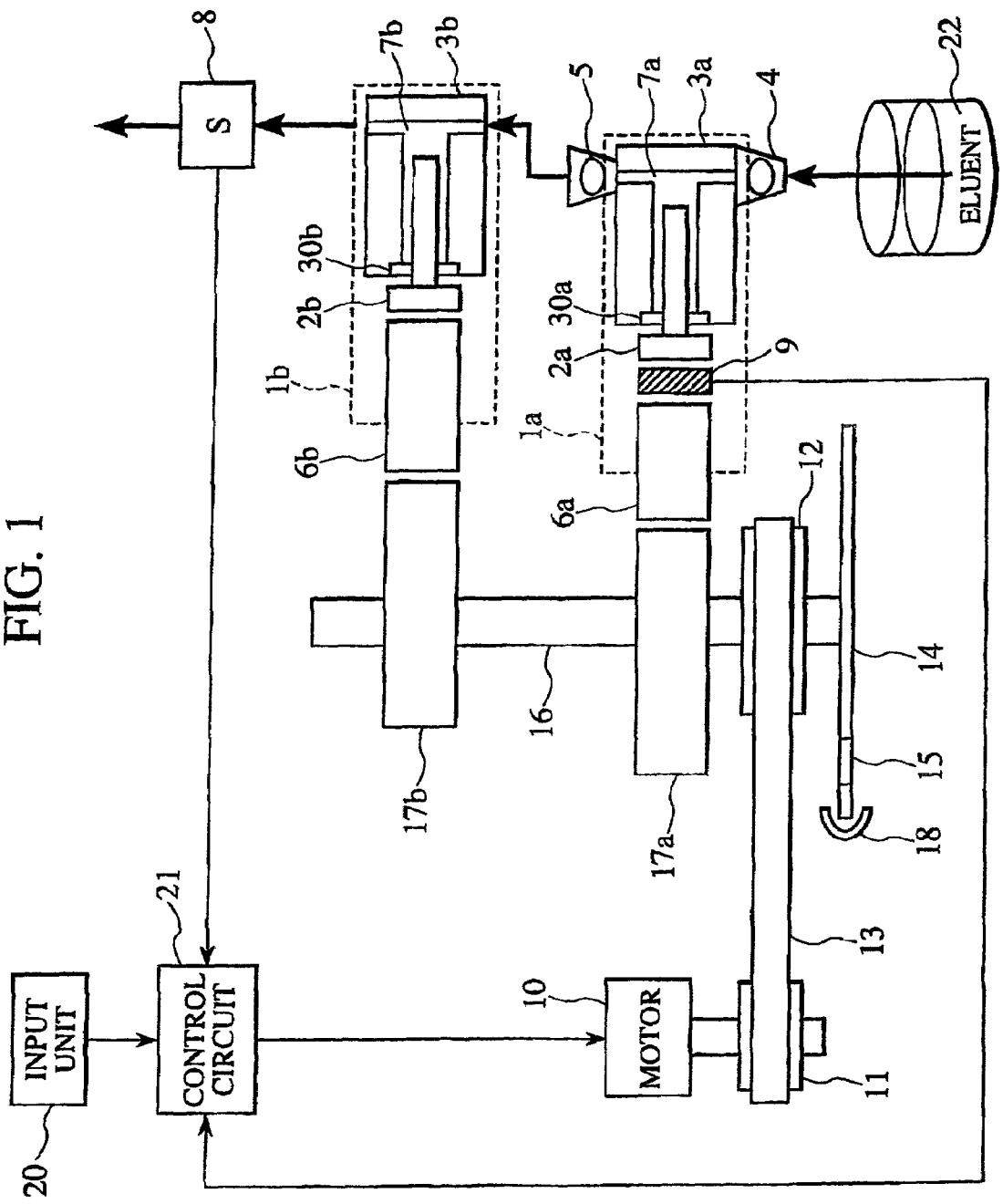
FIG. 1 schematically shows a solvent delivery device where the present invention is embodied.

FIG. 1 shows one embodiment of a solvent delivery device of the present invention. A rotary shaft 16 has cams 17a and 17b set thereon. The rotary shaft 16 has also a pulley 12 set thereon at an end thereof. From a pulley 12 fixed to the motor 10, the rotary motion of the motor 10 is transmitted to the rotary shaft 16 via a belt 13 and the pulley 12. In addition, a disk member 14 having a slit 15 formed therethrough is fixed to the rotary shaft 16. The cam positions of the cams 17a and 17b are detected by detecting the slit 15 through a cam position detecting sensor 18.

With its base end in contact with the cam 17a, a slider 6a reciprocates. A load sensor 9 is disposed at the other end of the slider 6a. The non-wetted end of a plunger 2a is disposed perpendicular to the load-sensing surface of the load sensor 9. A slider 6b also reciprocates with its base end in contact with the cam 17b. Opposite to the cam 17b, a plunger 2b is disposed in association with the slider 6b.

The pump head 3a of a plunger pump 1a has check valves 4 and 5 provided respectively in the inlet and outlet thereof. The plunger 2a is provided within the pump chamber 7a of the pump head 3a. The plungers 2a and 2b are respectively provided with plunger seals 30a and 30b for preventing leakage. When the wetted end of the reciprocating plunger 2a is moved to the cam 17a side, eluent 22 is charged into the pump chamber 7a from the check valve 4. Then, when the wetted end of the plunger 2a is moved to the pump head 3a side, the eluent 22 is compressed in the pump chamber 7a and discharged from the check valve 5. Since the check valves 4 and 5 do not open until the inlet eluent pressure becomes equal to the outlet eluent pressure, the compressed eluent 22 can be delivered always in a given direction.

The pump head 3b of a plunger pump 1b has the plunger 2b provided in the internal pump chamber 7b thereof. The plunger 2b reciprocates. When the wetted end of the plunger 2b is moved to the cam 17b side, eluent 22 is charged into the pump chamber 7b from the pump head 3a side. Then, when the wetted end of the plunger 2b is moved to the pump head 3b side, the eluent 22 is compressed in the pump chamber 7b and discharged to a pressure sensor 8 side. By the check valve 5, the eluent 22 can be delivered always in a given direction.

The pressure sensor 8 constantly measures the pressure of the eluent 22 discharged from the pump chamber 7b. The measured pressure is converted to an electrical signal and reported to a control circuit 21 which controls the motor drive. The load sensor 9 constantly measures the quantity of load which acts on the plunger 2a. The load quantity is converted to an electrical signal and reported to the control circuit 21. The control circuit 21 is connected to an input unit 20 for entering operating commands and necessary information.

Figure 3:
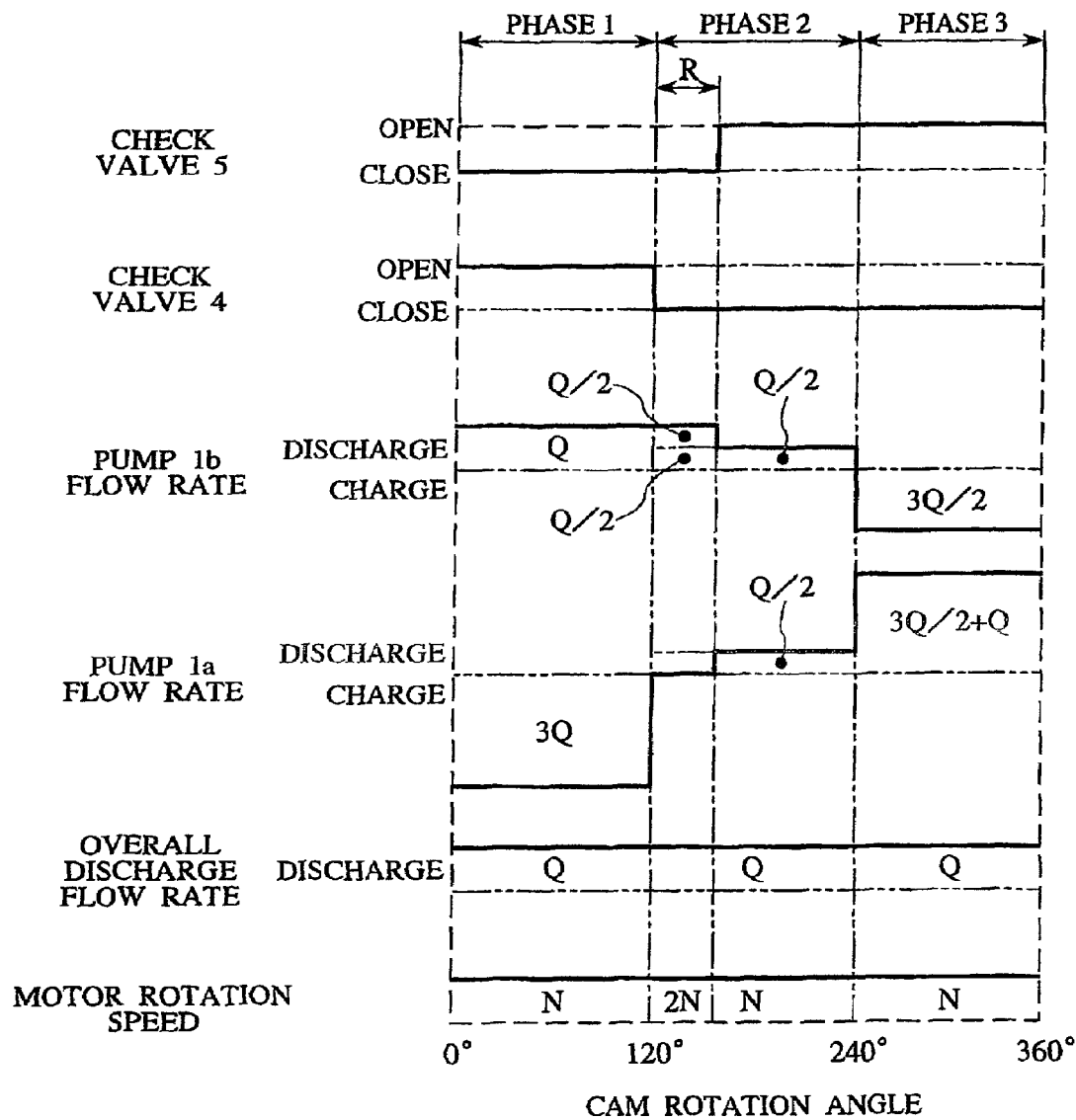
FIG. 3 is an exemplary graph showing relations among the opening/closing of check valves, pump flow rates, overall discharge flow rate, and motor rotation speed during each delivery cycle of the solvent delivery device of the present invention.

FIG. 3 shows exemplary reciprocating motions of the plungers. FIG. 3 indicates relations among the opening and closing of the check valves 4 and 5, the charge and discharge flow rates of the plunger pumps 1a and 1b, and the overall discharge flow rate of the solvent delivery device. One reciprocating cycle of the plungers for eluent delivery is divided into three phases.

In phase 1, the check valve 4 is opened and the check valve 5 is closed so that the plunger pump 1a is charged with the eluent 22 and only the plunger pump 1b discharges the eluent 22.

In the compression period R of phase 2, the check valves 4 and 5 are closed so that the eluent 22 charged into the plunger pump 1a is compressed and only the plunger pump 1b discharges the eluent 22 during the compression. If the eluent 22 charged into the plunger pump 1a is compressed to the discharge pressure, the check valve 5 is opened with the check valve 4 closed and consequently both plunger pumps 1a and 1b discharge the eluent 22.

In phase 3, the check valve 4 is closed and the check valve 5 is opened so that only the plunger pump 1a discharges the eluent 22 and the plunger pump 1b is charged with the eluent 22 discharged from the plunger pump 1a.

Depending on the discharge pressure from the solvent delivery device, the length of the eluent 22 compression period R is changed. For delivery at high pressure, the compression period R is set long. For delivery at low pressure, the compression period R is set short.

On the assumption that the quantity of eluent 22 to be delivered per unit time is set to Q, the following describes the compression period R. In the compression period R, the check valve 5 is closed so that only the plunger pump 1b delivers at a discharge flow rate of Q while the eluent charged into the plunger pump 1a is compressed. The cam profile of the plunger pump 1b for the compression period R is designed so that the discharge flow rate is reduced from Q to ½Q. However, the discharge flow rate from the plunger pump 1b is set to Q by temporally doubling the rotation speed N of the motor 10. This intends to keep the overflow flow rate at Q by doubling the rotation speed N of the motor 10 during the compression period. Otherwise, in the compression period R, the overall flow rate would fall to Q/2 since only the plunger pump 1b discharges and the plunger pump 1a does not discharge. At the end of the compression period R, the rotation speed of the motor 10 is returned to the regular delivery rotation speed N from 2N.

The quantity of load on the load sensor 9 while the check valve 5 is open after the end of the compression R is stored in the control circuit 21. In the subsequent reciprocating cycle of the plungers, if the quantity of load on the load sensor 9 reaches the load quantity stored in the control circuit 21, the control circuit 21 terminates the compression period R by returning the rotation speed of the motor 10 to N from 2N. Since the load sensor is calibrated by the pressure sensor, it is possible to accurately terminate the compression period R immediately after the check valve 5 is opened, resulting in pulsation-free delivery.

If a pulsation occurs in the first delivery cycle, the rotation speed of the motor 10 is compensated for the difference between the pressure measured by the pressure sensor 8 and the target pressure in order to keep the pressure constant. The quantity of load acting while the check valve 5 is open is measured by the load sensor 9 and stored in the control circuit 21 as the load value to end the compression period R. Even in this case, since the load sensor is calibrated by the pressure sensor, it is possible to accurately terminate the compression period R immediately after the check valve 5 is opened, resulting in pulsation-free delivery.

The following provides a description of a gradient solvent delivery application where the target flow rate is changed with time. If the target flow rate changes, the control circuit 21 changes the rotation speed of the motor 10 based on the pressure which is constantly measured by the pressure sensor 8. Changing the rotation speed of the motor 10 changes the quantity of load on the load sensor 9 while the check valve 5 is open, with the result that a new load quantity is stored in the control circuit 21. In the subsequent delivery cycles, since the compression period R is terminated when the quantity of load on the load sensor 9 reaches the new load quantity stored in the control circuit 21, pulsation-free delivery can be done by terminating the compression period R immediately after the check valve 5 is opened. The length of the compression period R is calculated and determined based on the flow rate and discharge pressure as the case may be. Gradient solvent delivery is performed in this manner.

In phase 1 of the example in FIG. 3, with the check valve 4 opened and the check valve 5 closed, the plunger pump 1a is charged with the eluent 22 at a flow rate of 3Q and only the plunger pump 1b discharges the eluent 22 at a flow rate of Q.

In the compression period R of phase 2, with the check valves 4 and 5 closed, while the eluent 22 charged into the plunger pump 1a is compressed, only the plunger pump 1b discharges the eluent 22 at a flow rate of Q during the compression. When the eluent charged into the plunger pump 1a is compressed to the discharge pressure (end of the compression period R), the check valve 5 is opened with the check valve 4 kept closed so that both plunger pumps 1a and 1b discharge respectively at a flow rate of Q/2.

In phase 3, with the check valve 4 closed and the check valve 5 opened, only the plunger pump 1a discharges the eluent 22 at a flow rate of 3Q/2+Q and the plunger pump 1b is charged at a flow rate of 3Q/2 with the eluent 22 discharged from the plunger pump 1a.

In the embodiment of the present invention, since no pressure sensor is needed between the plunger pump 1a and the plunger 1b thanks to the use of a load sensor, the volume of eluent to be compressed can be reduced and consequently it is possible to deliver eluent at very high pressure.

In addition, although the signal from the load sensor generally includes errors due to various frictions, accurate eluent delivery is possible since calibration is performed based on the pressure sensor during each reciprocating cycle of the plungers.

As mentioned so far, the present invention attains the object of providing a stable solvent delivery device capable of delivering eluent both at high pressure and at a constant flow rate through the following means which uses a pressure sensor and a load sensor. The pressure of eluent discharged from the discharge side pump chamber is constantly measured by the pressure sensor and reported to a control circuit. Based on the measured pressure, the reciprocating speed of the plungers is controlled by the control circuit so that the discharge pressure of eluent is kept constant. The quantity of load acting on the plunger in the charge side pump chamber is constantly measured by the load sensor and reported to the control circuit. To keep the discharge pressure constant, the motor rotation is controlled so as to secure that the eluent charged into the charge side pump chamber is compressed to the discharge pressure. While the outlet check valve is open, the internal pressure of the charge side pump chamber is equal to the discharge pressure. The signal obtained from the load sensor is calibrated based on the discharge pressure signal from the pressure sensor. The motor rotation is controlled by using the calibrated signal. Note that various modifications and applications are possible within the scope of the technical concept of the present invention. For example, it is possible to improve the analysis accuracy of liquid chromatographs and spectrophotometers by incorporating the above-mentioned solvent delivery device of the present invention in such analytical systems.

What is claimed is:

1. A solvent delivery device comprising:
   a plurality of plungers which reciprocate in respective pump chambers;
   a motor which is used to reciprocate the plungers;
   a control unit which controls operation of the motor;
   check valves which are respectively disposed at an eluent inlet and an eluent outlet of a first pump chamber of the pump chambers;
   a first sensor which measures a quantity of load received by the plunger of the first pump chamber; and
   a second sensor which measures a pressure of the eluent discharged from a second pump chamber whose eluent inlet is connected to the eluent outlet of the first pump chamber.

2. The solvent delivery device according to claim 1, further comprising:
   a cam which reciprocates the plunger of the first pump chamber; and
   wherein the first sensor is arranged between the cam and the plunger of the first pump chamber.

3. The solvent delivery device according to claim 1, wherein the eluent discharge flow rate is controlled based on output signals of the first sensor and the second sensor.

4. A solvent delivery device according to claim 3,
   wherein, eluent compression is terminated when the relation between the signal value from the first sensor while the outlet check valve of the first pump chamber is open and the signal value from the first sensor while the eluent is compressed inside the first pump chamber come to satisfy a predetermined condition relation.

5. A solvent delivery device according to claim 1, wherein the first sensor is calibrated using an output signal of the second sensor.

6. An analytical system comprising:
   a solvent delivery device according to claim 1;
   a sample introduction device; and a detector;
   wherein by using the eluent delivered from the solvent delivery device, a sample is moved directly or indirectly from the sample introduction device to the detector.

7. A liquid chromatograph comprising:
   a solvent delivery device according to claim 1;
   a sample introduction device;
   a separation column;
   a detector; and
   a data processor;
   wherein eluent is delivered to the separation column from the solvent delivery device, a sample is introduced into the separation column by the sample introduction device, components of the sample separate from each other in the separation column, the separated sample components are detected by the detector, and signals concerning the detected sample components are processed by the data processor as predetermined.

8. A solvent delivery device according to claim 1, wherein the motor is controlled based on output signals of the first sensor and the second sensor.

* * * * *